United States Patent
Lim

(10) Patent No.: US 10,159,543 B2
(45) Date of Patent: Dec. 25, 2018

(54) METHOD OF FABRICATING CUSTOM DENTAL CORRECTION DEVICE, AND CUSTOM DENTAL CORRECTION DEVICE FABRICATED BY SAME

(71) Applicant: INDUSTRY-ACADEMIC COOPERATION FOUNDATION CHOSUN UNIVERSITY, Gwangju (KR)

(72) Inventor: Sung Hoon Lim, Gwangju (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 15/128,288

(22) PCT Filed: May 19, 2015

(86) PCT No.: PCT/KR2015/004986
§ 371 (c)(1),
(2) Date: Sep. 22, 2016

(87) PCT Pub. No.: WO2015/178655
PCT Pub. Date: Nov. 26, 2015

(65) Prior Publication Data
US 2017/0105814 A1    Apr. 20, 2017

(30) Foreign Application Priority Data
May 22, 2014    (KR) .................. 10-2014-0061644

(51) Int. Cl.
*A61C 7/00*     (2006.01)
*A61C 7/28*     (2006.01)
(Continued)

(52) U.S. Cl.
CPC .............. *A61C 7/002* (2013.01); *A61C 7/148* (2013.01); *A61C 7/20* (2013.01); *A61C 7/28* (2013.01)

(58) Field of Classification Search
CPC ................................. A61C 7/002; A61C 7/28
(Continued)

(56) References Cited

U.S. PATENT DOCUMENTS 3,043,007 A * 7/1962 Wallshein ................ A61C 7/12
433/20
4,014,096 A * 3/1977 Dellinger ................. A61C 7/12
433/24
(Continued)

FOREIGN PATENT DOCUMENTS

KR    10-2002-0072318 A    9/2002
KR       10-0647356 B1    11/2006
(Continued)

OTHER PUBLICATIONS

International Search Report for PCT/KR2015/004986.

*Primary Examiner* — Matthew Nelson
(74) *Attorney, Agent, or Firm* — The PL Law Group, PLLC

(57) ABSTRACT

A method of fabricating a customized orthodontic appliance includes a setup model forming step of preparing a setup model corresponding to teeth after ideal orthodontic treatment for a patient, an arch wire forming step of preparing an arch wire corresponding to a dental arch of the setup model while being disposed to closely approach tooth surfaces of teeth of the setup model, and an orthodontic bracket forming step of forming a bracket body corresponding to each of the teeth with reference to the arch wire. Through this, the customized orthodontic appliance capable of minimizing the distance between the tooth surface and the arch wire to accurately perform the ideal orthodontic treatment is fabri-
(Continued)

cated. Also, convenience and accuracy of procedure is improved, and irritating sensation in the oral cavity is minimized.

12 Claims, 18 Drawing Sheets

(51) Int. Cl.
*A61C 7/14* (2006.01)
*A61C 7/20* (2006.01)

(58) Field of Classification Search
USPC .................................................. 433/8–24
See application file for complete search history.

(56) References Cited

U.S. PATENT DOCUMENTS

| | | | | |
|---|---|---|---|---|
| 4,354,833 | A * | 10/1982 | Fujita ...................... | A61C 7/20 433/20 |
| 5,454,717 | A * | 10/1995 | Andreiko ................ | A61C 7/00 433/24 |
| 5,474,448 | A * | 12/1995 | Andreiko ................ | A61C 7/00 433/24 |
| 7,811,087 | B2 * | 10/2010 | Wiechmann ........... | A61C 7/002 433/9 |
| 8,057,226 | B2 * | 11/2011 | Wiechmann ........... | A61C 7/002 433/16 |
| 2004/0214128 | A1 * | 10/2004 | Sachdeva ................ | A61C 7/00 433/24 |
| 2004/0214129 | A1 * | 10/2004 | Sachdeva ................ | A61C 7/00 433/24 |
| 2004/0265770 | A1 * | 12/2004 | Chapoulaud ............ | A61C 7/00 433/24 |
| 2009/0017411 | A1 * | 1/2009 | Pospisil .................. | A61C 7/28 433/9 |
| 2009/0291417 | A1 * | 11/2009 | Rubbert .................. | A61C 7/00 433/215 |
| 2012/0270175 | A1 * | 10/2012 | Huge ...................... | A61C 7/34 433/14 |
| 2013/0252194 | A1 * | 9/2013 | Hagelganz .............. | A61C 7/12 433/9 |

FOREIGN PATENT DOCUMENTS

| | | |
|---|---|---|
| KR | 10-0845600 B1 | 7/2008 |
| KR | 10-0916181 B1 | 9/2009 |
| KR | 10-2012-0101086 A | 9/2012 |
| KR | 10-2013-0016526 A | 2/2013 |
| KR | 10-2013-0125132 A | 11/2013 |

* cited by examiner

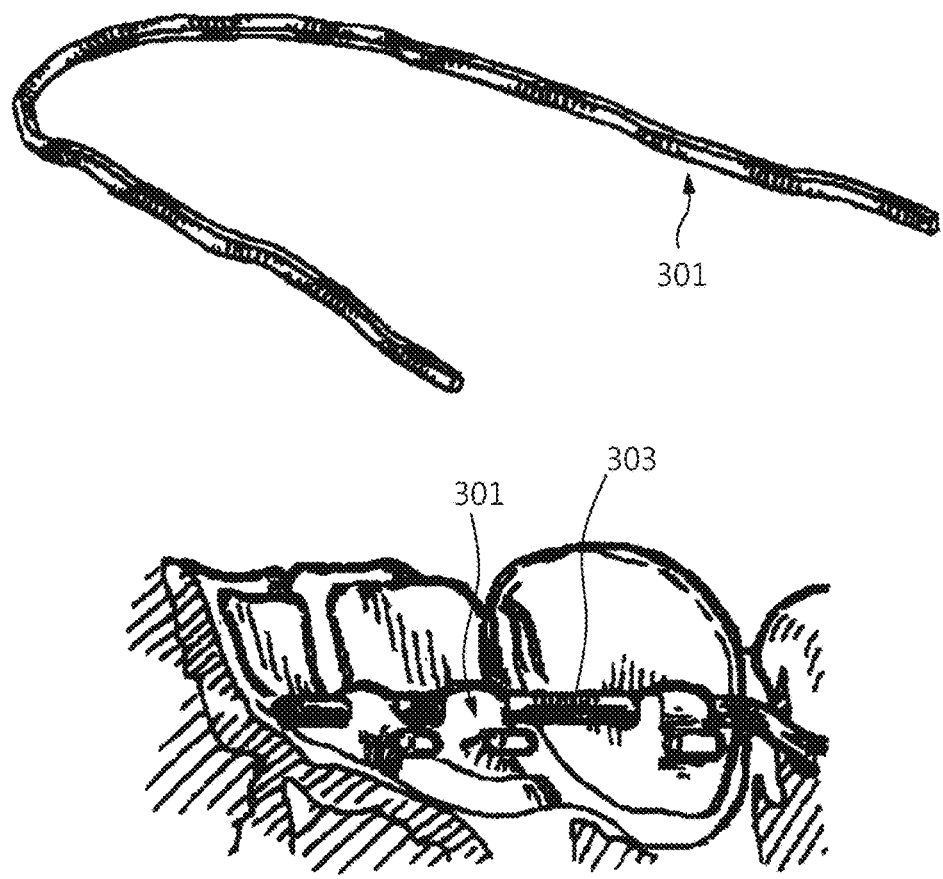

US 10,159,543 B2

METHOD OF FABRICATING CUSTOM DENTAL CORRECTION DEVICE, AND CUSTOM DENTAL CORRECTION DEVICE FABRICATED BY SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/004986, filed May 19, 2015, which claims priority to the benefit of Korean Patent Application No. 10-2014-0061644 filed in the Korean Intellectual Property Office on May 22, 2014, the entire contents of which are incorporated herein by reference.

TECHNICAL FIELD

The present invention relates to a method of fabricating a custom dental correction device and a custom dental correction device fabricated by the same, and more particularly, to a method of fabricating a customized orthodontic appliance capable of perfectly performing ideal orthodontic treatment in correspondence to shapes of a tooth and teeth of an individual patient and minimizing irritating sensation in an oral cavity and a customized orthodontic appliance fabricated by the same.

BACKGROUND ART

In general, the orthodontic treatment is a dental procedure for moving maloccluded teeth to ideally occluded positions and performed by using an orthodontic appliance.

The orthodontic method is classified into a labial orthodontic method in which the orthodontic appliance is bonded to a tooth surface facing the outside of an oral cavity to perform the orthodontic treatment and a lingual orthodontic method in which the orthodontic appliance is bonded to a tooth surface facing the tongue to perform the orthodontic treatment. In recent years, the lingual orthodontic method by which the orthodontic appliance is not exposed to the outside is preferred.

A conventional orthodontic appliance used for the orthodontic treatment includes a bracket bonded to teeth of a patient and an arch wire ligated to a slot defined in the bracket to provide pulling force for moving the teeth respectively to orthodontic positions.

The orthodontic treatment using the conventional orthodontic appliance is performed such that the mass-produced bracket having a predetermined shape is bonded to the teeth of the patient, and then the arch wire is bent to correspond to an ideal dental arch (curvature of teeth) and ligated to a bracket slot.

However, since the above-described conventional orthodontic appliance includes the bracket that is mass-produced to have the predetermined shape without considering shapes of the tooth and teeth of the patient, and bonding of the bracket to the teeth of the patient and fitting to form the arch wire to the ideal dental arch shape are dependent on a competence level of an operator, the bonding of the bracket to an exact position of the tooth and the forming of the arch wire at an exact curvature are extremely difficult.

Thus, when the conventional orthodontic appliance is used, successful orthodontic treatment is not guaranteed To improve the above-described problem of the conventional orthodontic appliance, various kinds of orthodontic appliances and methods thereof have been developed. In recent years, the orthodontic appliance customized to the patient based on rapid prototyping and the method of fabricating the same have been developed.

Briefly referring to technical contents related to the orthodontic appliance fabrication disclosed in Korean Patent Publication No. 10-2012-0101086, an orthodontic setup model showing the predicted post-treatment is fabricated, and then a base to be bonded to each of tooth surfaces is numerically designed to be fabricated by using the rapid prototyping.

Thereafter, a mass-produced bracket body having a linear bracket slot is fixed to an appropriate position of the base, and the arch wire is fabricated by the numerical design to be inserted into the bracket slot and then fabricated to correspond to a curvature of the dental arch after the orthodontic treatment.

Since, in the orthodontic appliance fabricated as described above, the base is relatively accurately fit to the tooth surface after the ideal orthodontic treatment for the patient, and the arch wire has the curvature corresponding to the dental arch after the orthodontic treatment, the orthodontic treatment is satisfactorily performed relative to the conventional orthodontic treatment procedure.

However, the above-described conventional orthodontic appliance has problems as follows.

Since the orthodontic bracket, as a mass-produced stock bracket, has the linearly processed bracket slot into which the arch wire is inserted, the linearized slot may not accurately correspond to the curvature of the arch wire fabricated to fit to the dental arch after the orthodontic treatment for the patient.

Thus, when the arch wire is inserted into the bracket slot, the linearized slot is not shape-matched to the curvature of the arch wire. In detail, in case of a labial orthodontic treatment, the arc wire substantially contacts both end areas in a longitudinal direction of the bracket slot, and in case of a lingual orthodontic treatment, the arc wire substantially contacts one point of the bracket slot.

Due to this, the arch wire having the curvature may not completely close-contact the linearized slot not to expect the exact pulling force and pulling position. In particular, the pulling force for orthodontic-treating a protruding angle of the tooth may not be provided. This may cause a serious problem in ideal orthodontic treatment.

When the base is custom-fabricated by using the setup model showing post-treatment occlusion, the base may be bonded to an exact position of the tooth without much difficulty. However, since the body portion including the bracket slot still uses a mass-produced stock product and is assembled to the base, a final bracket profile is raised and the bonding of the base at the exact position is difficult.

As described above, when the bracket profile is raised, irritation sensation increases as a volume of the orthodontic bracket increases, and a distance between the tooth surface (surface of the tooth) and the wire increases to reduce adjustability in tooth position.

Orthodontic force applied to the tooth is applied to the orthodontic bracket instead of a center of gravity or a center of resistance. The above-described orthodontic force that does not pass through the center of resistance of the tooth unavoidably generates rotational moment. As a result of this rotational moment, the teeth ligated by the arch wire rotate with respect to a portion around the bracket slot. When explained in more detail with reference to FIG. 1, when the rotational moment is unintentionally generated by accompanying movement of another tooth or rotational moment M is applied to an orthodontic bracket 201 by applying torque bend or third order bend to an arch wire 203 because a degree of buccolingual inclination of a tooth T has a problem, the tooth T rotates with respect to the arch wire 203 inserted into the bracket slot, and as a result, the degree of buccolingual inclination of the tooth and also a vertical height of an end (incisal edge or cusp tip) of the tooth may be changed. As the bracket slot is spaced further away from the tooth surface (i.e., as the bracket profile is raised), the above-described problem becomes further serious.

In particular, in case of the lingual orthodontic treatment, when a stock bracket is used instead of a customized bracket, the arch wire 203 that is the rotational center of the tooth T is spaced further away from the tooth surface to significantly increase height difference between incisal edges of the tooth T after/before the orthodontic treatment as in FIG. 1.

Accordingly, as the distance from the tooth surface to the arch wire 203 increases, an amount additionally height-adjusted remarkably increases when the degree of buccolingual inclination of the tooth T is adjusted.

Also, when the distance from the tooth surface to the arch wire 203 increases, since the orthodontic force is applied further away from the central point or the center of resistance of the tooth T as the distance from the tooth surface or the incisal edge, which moves even when horizontal or vertical movement is performed, to the arch wire 203 increases, movement accompanied by the rotational moment instead of only horizontal or vertical movement occurs, and this rotational moment is difficult to be appropriately adjusted, thereby hardly performing the ideal orthodontic treatment.

Accordingly, it is desired that the distance between the bracket slot, into which the arch wire 203 is mounted, and the tooth surface is minimized when the orthodontic bracket 201 is fabricated.

On the other hand, as another related art, a technique regarding 'MODULAR SYSTEM FOR CUSTOMIZED ORTHODONTIC APPLIANCES' is disclosed in Korean Patent Publication No. 10-0647356 as in FIG. 2.

This patent technique imports an orthodontic bracket 301 in which a linear bracket slot is pre-formed from an established library of a virtual bracket body pre-stored as a digital shape data in a computer to align the orthodontic bracket 301, and then an arch wire 303 corresponding to the alignment of the orthodontic bracket is designed.

Here, since the orthodontic bracket is firstly aligned and then the arch wire is designed, as a result, the arch wire is spaced away from the tooth surface to increase a height of the bracket profile and the irritating sensation. As above-described with reference to FIG. 1, the distance between the tooth surface and the arch wire increase to reduce the adjustability of the tooth position by the orthodontic appliance.

Also, in this related art, since the bracket body having the linear bracket slot is imported from the established library to align the orthodontic bracket, the bracket slots are separately aligned instead of aligned along the arch wire that is continuously implemented, and then a wire for orthodontic treatment (arch wire) is formed such that a distance between the neighboring linear bracket slots are connected by a separate linear line.

That is, as described in FIGS. 3A and 3B, the arch wire 303 having a shape in which the orthodontic bracket 301 is aligned and then the linear line of the bracket slot and the linear line corresponding to a region between the orthodontic brackets 301 are connected to each other and the orthodontic bracket 301 having a shape in which the arch wire 303 is bent to have a linear section corresponding to a region between a linear section corresponding to the slot and the orthodontic bracket 301 are fabricated together to be provided.

In case of the above-described method, when the mounting position of the arch wire 303 is slightly deviated from an intended position, a relationship between the arch wire and the orthodontic bracket 301 may change. Accordingly, the teeth may be aligned on positions different from the positions intended on the basis of the relationship. Also, in the malocclusion in a state in which a protruding tooth exists, the orthodontic bracket bonded to the tooth moves along the arch wire to straighten the protruding tooth, and when a bent portion between the linear lines is disposed in the slot, severe friction is generated on the portion, so that gliding movement of the wire in the slot becomes difficult and thus the teeth alignment is stopped or slowed.

That is, when the arch wire 303 is accurately mounted on the pre-intended position as illustrated in FIG. 4A, the customized arch wire 303 that is bent at every portion between the orthodontic brackets 301 may be accurately mounted. However, when the arch wire 303 is mounted to be slightly deviated (e.g. 1 mm) to the right side (or left side) from the intended position as in FIG. 4B, as a portion 'a' indicated by a circle and an arrow in FIGS. 4A and 4B moves, the arch wire 303 is not matched to the bracket slot. Here, when the arch wire 303 is inserted into the bracket slot, the tooth moves to an undesired position, so that the orthodontic treatment is inaccurately performed or the bent portion is disposed in the bracket slot, thereby generating severe friction to stop or slow the tooth movement Also, since each of the bracket slots is linearly formed, like the above-described related art, in case of the labial orthodontic treatment, the arch wire 303 substantially contacts both end areas of the bracket slot in the longitudinal direction, and in case of the lingual orthodontic treatment, the arch wire 303 substantially contacts one point of the bracket slot.

Thus, as the arc wire 303 may not completely close-contact the bracket slot, the exact pulling force and pulling position may not be expected to hardly perform the ideal orthodontic treatment.

SUMMARY

The purpose of the present invention is to provide a method of fabricating a customized orthodontic appliance capable of minimizing a distance between a tooth surface and an arch wire to accurately perform ideal orthodontic treatment and a customized orthodontic appliance fabricated by the same.

Also, the purpose of the present invention is to provide a method of fabricating a customized orthodontic appliance capable of significantly improving the convenience and accuracy of procedure and minimizing irritating sensation in an oral cavity and a customized orthodontic appliance fabricated by the same.

The above-described purpose of the present invention is accomplished by a method of fabricating a customized orthodontic appliance, the method including: a setup model forming step of preparing a setup model corresponding to teeth after ideal orthodontic treatment for a patient; an arch wire forming step of preparing an arch wire corresponding to a dental arch of the setup model while being disposed to closely approach tooth surfaces of teeth of the setup model;

and an orthodontic bracket forming step of forming a bracket body which fills the gap between the teeth and the arch wire.

Here, the orthodontic bracket forming step may include: a bracket body block forming step of forming a single bracket body block along an entire section of the arch wire; and a bracket body forming step of forming the bracket bodies respectively corresponding to each tooth from the bracket body block.

Also, the bracket body forming step may include steps of: forming a bracket cutting block having a body forming structure corresponding to each of the bracket bodies; and cutting the bracket body block by using the bracket cutting block to form each of the bracket bodies.

Also, the method may further include a step of removing a portion corresponding to the arch wire from the bracket body block to form a bracket slot.

Also, the method may further include a step of removing a portion corresponding to the arch wire from the bracket body to form a bracket slot.

Meanwhile, the orthodontic bracket forming step may include: a primitive bracket body alignment step of aligning primitive bracket bodies at a position corresponding to the arch wire disposed to closely approach the tooth surface of each of the teeth; and a slot forming step of forming a slot corresponding to the arch wire in each of the primitive bracket bodies.

Also, the arch wire may be disposed to closely approach the tooth surface in a range of 0.01 mm to 0.3 mm.

Also, the method may further include a step of forming at least one of a ligature groove, to which a ligature wire for fixing the real arch wire is ligated, or a bracket wing in the bracket body.

Also, the method may further include a step of removing a portion at which the bracket body overlaps the setup model to form a bonding surface corresponding to the tooth surface of each of the teeth of the setup model on a side of each of the bracket bodies, which faces the tooth surface.

Also, the method may further include a step of forming a separate bracket base corresponding to the tooth surface on a side of each of the bracket bodies, which faces the tooth surface.

Here, a minimum distance between the arch wire and the tooth surface may be less than a thickness of the bracket base.

Also, the method may further include an arch wire insertion path forming step of removing a portion in which the thickness of the bracket base intrudes to the slot.

Also, the method may further include a ligature member insertion path forming step of removing a portion in which the thickness of the bracket base intrudes to a ligature member insertion path formed by the ligature groove or the bracket wing.

Meanwhile, the above-described purpose of the present invention is accomplished by a customized orthodontic appliance fabricated by a method of fabricating a customized orthodontic appliance according to another embodiment.

Meanwhile, the above-described purpose of the present invention is accomplished by a customized orthodontic appliance fabricated by a method of fabricating a customized orthodontic appliance according to another embodiment, the customized orthodontic appliance including an arch wire closely approaching to a setup model corresponding to the teeth after ideal orthodontic treatment for a patient; and a bracket body having a slot which has a curved labial wall corresponding to the curvature of the arch wire, and a straight lingual wall which was linearized from the curve corresponding to the curvature of the arch wire.

Here, the arch wire may be disposed to closely approach the tooth surface in a range of 0.01 mm to 0.3 mm.

Also, a surface of the bracket body, which faces the tooth surface, may be provided as a bonding surface to be bonded to the tooth surface.

Also, at least one of a ligature groove or a bracket wing, to which a ligature wire for fixing the real arch wire is ligated, may be provided in the bracket body.

Alternatively, a separate bracket base corresponding to the tooth surface may be disposed on a side of each of the bracket bodies, which faces the tooth surface.

Here, as portions in which the bracket base intrudes to an arch wire insertion path and a ligature member insertion path are removed to secure the arch wire insertion path and the ligature member insertion path, the arch wire insertion path and the ligature member insertion path may not be blocked by the bracket base.

Also, the arch wire may be fabricated by using a shape of the arch wire formed in the arch wire forming step of claim 1.

According to the present invention, provided are the method of fabricating the customized orthodontic appliance capable of minimizing the distance between the tooth surface and the arch wire to accurately perform the ideal orthodontic treatment and the customized orthodontic appliance fabricated by the same.

Also, provided are the method of fabricating the customized orthodontic appliance capable of remarkably improving the convenience and accuracy of the procedure and minimizing the irritating sensation in the oral cavity and the customized orthodontic appliance fabricated by the same.

BRIEF DESCRIPTION OF THE DRAWINGS

FIGS. 1 to 4 are views for explaining a conventional orthodontic appliance.

DETAILED DESCRIPTION

Figure 5:
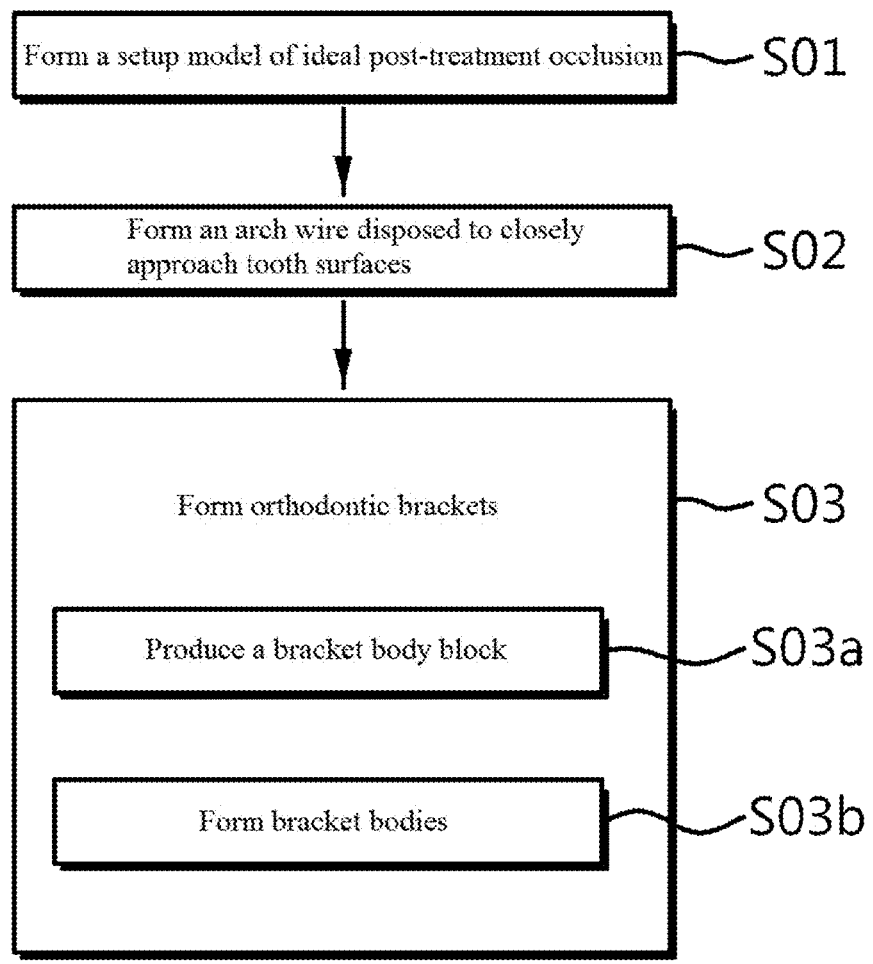
FIGS. 5 to 15 are views for explaining a method of fabricating an orthodontic appliance according to the present invention.

As illustrated in FIG. 5, a method of fabricating an orthodontic appliance according to the present invention includes: a setup model forming step S01 of preparing a setup model 10 showing post-treatment occlusion; an arch wire forming step S02 of preparing an arch wire 60 corresponding to a dental arch of the setup model 10 while being disposed to closely approach tooth surfaces of teeth of the setup model 10; and an orthodontic bracket forming step S03 of forming a bracket body 40 corresponding to each of the teeth of the setup model with reference to the arch wire 60.

The setup model forming step S01 is a step of preparing the setup model showing the post-treatment occlusion for the patient to be orthodontic treated. The setup model 10 may be prepared by using 3D scanning, computer-aided design, and rapid prototyping or the real setup model may be prepared by using a plaster cast.

Figure 6:
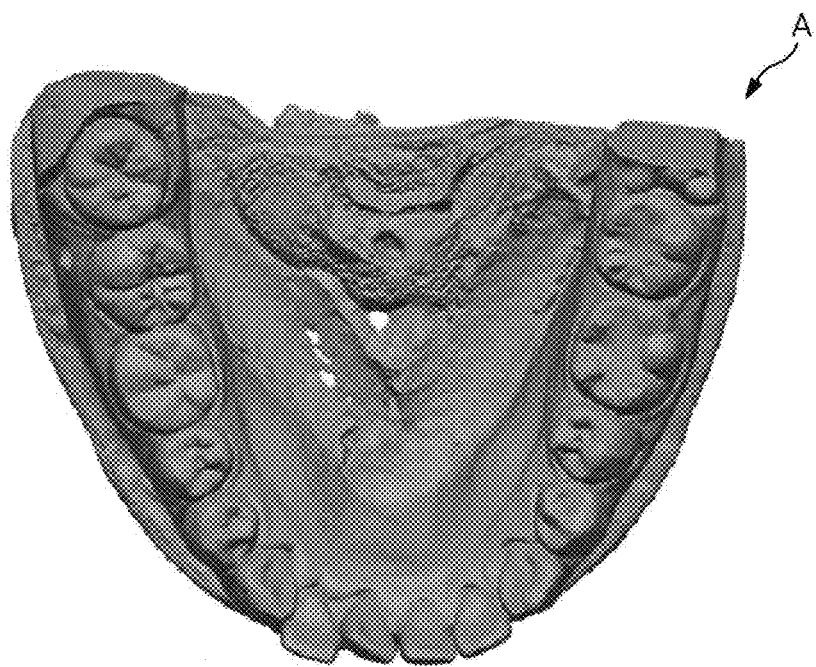
Figure 7:
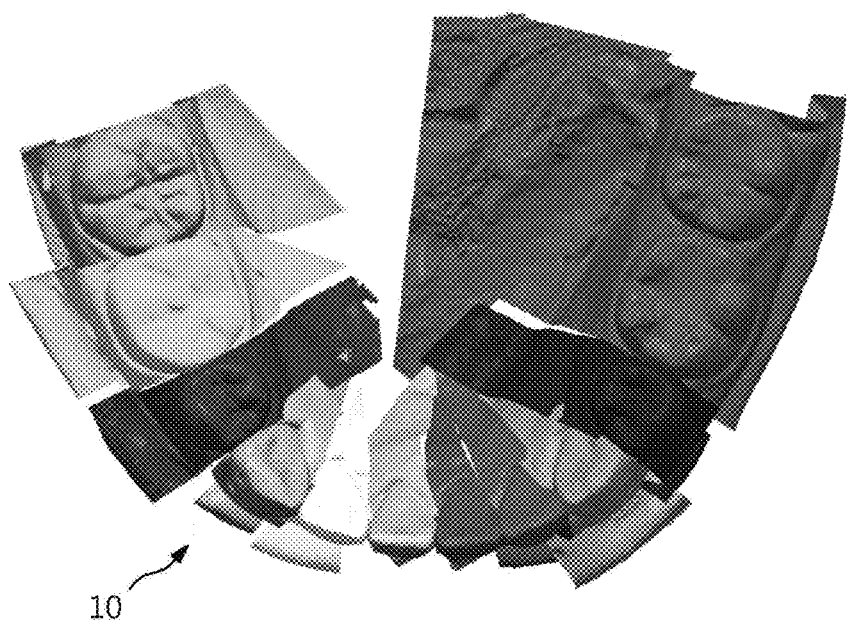

In case of 3D scanning, computer-aided design, and rapid prototyping, the oral cavity and the teeth before orthodontic treatment are 3D-scanned to acquire a 3D scan data A before the orthodontic treatment like FIG. 6. By using these 3D scan data, virtual 3D teeth before the orthodontic treatment are aligned to the teeth after the ideal orthodontic treatment to produce the virtual 3D setup model 10 showing the post-treatment occlusion like FIG. 7. Thereafter, the real setup model may be fabricated by using the rapid prototyping on the basis of the produced virtual setup model 10.

On the other hand, in case of the plaster cast, the real setup model may be manually fabricated by a skilled dental technician using plaster, and then the real plaster setup model is 3D-scanned to be used for forming of the arch wire 60 and the bracket body 40, which will be described later.

The arch wire forming step S02 is a step of preparing at least one arch wire 60 having a line corresponding to the dental arch (dental arch curvature or straight line) while being disposed to closely approach the tooth surface of the setup model 10. The arch wire 60 may be utilized to form a slot 43 that will be formed in the orthodontic bracket forming step S03 that will be described later and used as data for fabricating the real arch wire (not shown).

Figure 8:
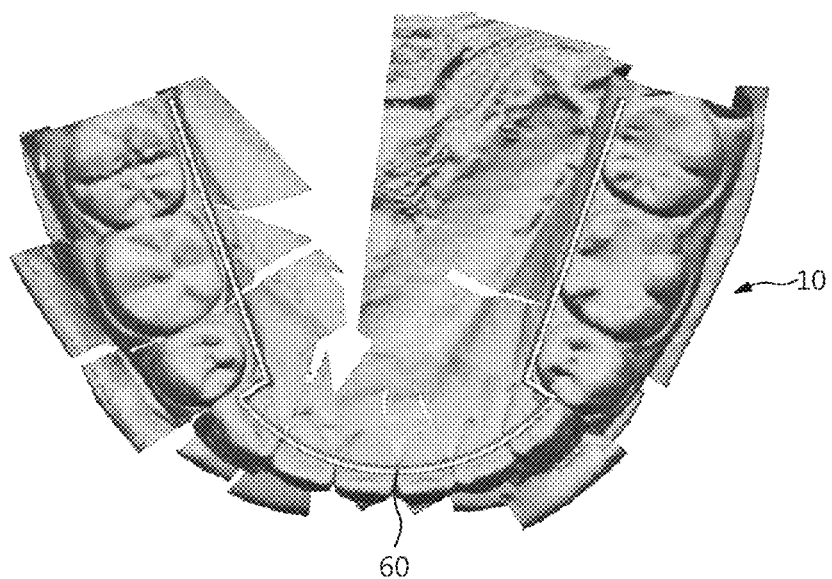

In lingual orthodontic appliance, like FIG. 8, the virtual 3D arch wire 60 having the teeth curvature or the teeth linear line, which are disposed to closely approach the tooth surface of the virtual setup model 10 on the computer may be produced, and then the virtual 3D arch wire 60 data may be used to fabricate the real arch wire (not shown). In case of a labial orthodontic appliance, FIGS. 17 and 18 may be referred.

Here, it is desirable that the arch wire 60 is disposed to maximally approach the tooth surface. In detail, a minimum gap between the tooth surface and the arch wire 60 is desirably 0.3 mm or less.

Figure 9:
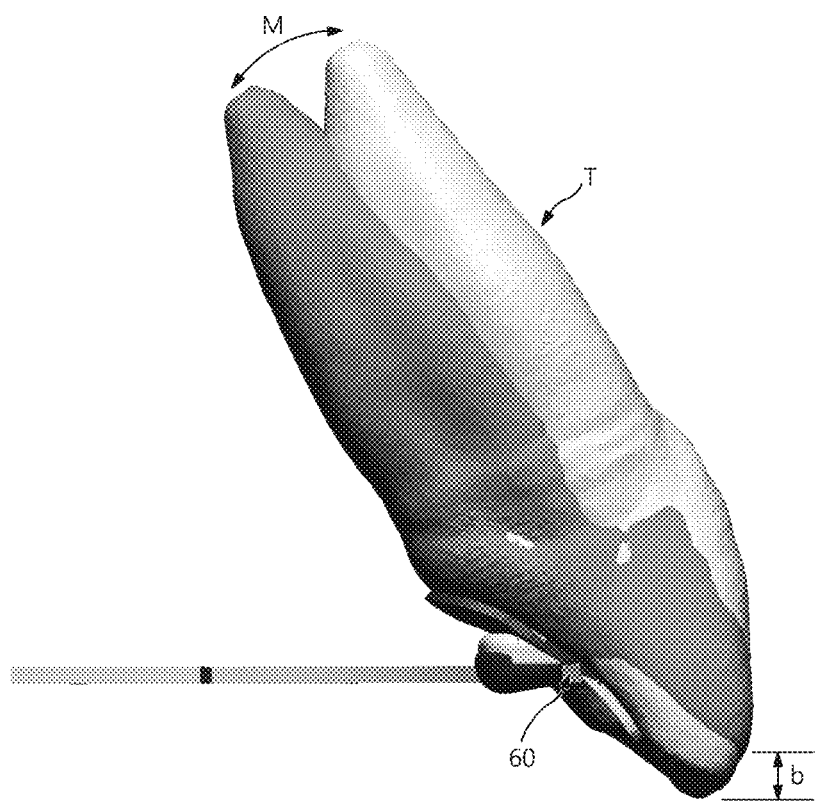

As described above, when the rotational moment is generated to rotate the teeth with the center of rotation at the arch wire 60 like the above-described related art, as in FIG. 9, the arch wire 60 is disposed to closely approach the tooth surface to minimize variation ('b' in FIG. 9) in height of an incisal edge of the tooth before/after the orthodontic treatment. Here, the distance from the tooth surface to the arch wire 60 is minimized to significantly reduce an amount to be additionally height-adjusted when a degree of buccolingual inclination of the tooth is adjusted.

By virtue of this, as when the tooth T horizontally and vertically moves, the distance between the tooth surface or the incisal edge and the arch wire 60 is minimized, like FIG. 9, orthodontic force is applied to a portion disposed adjacent to a central point or a center of resistance of the tooth to smoothly move the tooth T horizontally and vertically. Also, although the tooth T moves with rotational moment M accompanied, since the tooth T rotates with respect to a portion disposed further close to the tooth surface, unnecessary vertical and horizontal movement of the incisal edge and a cusp tip may be minimized to perform the ideal orthodontic treatment.

Figure 1:
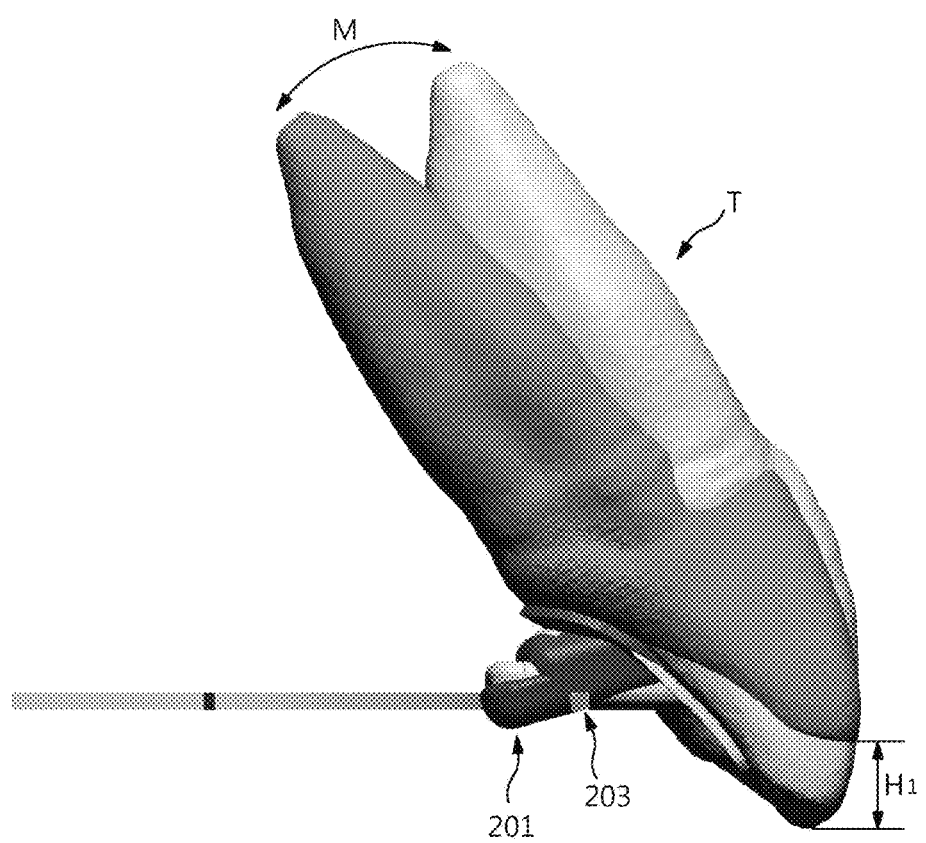
Figure 3A:
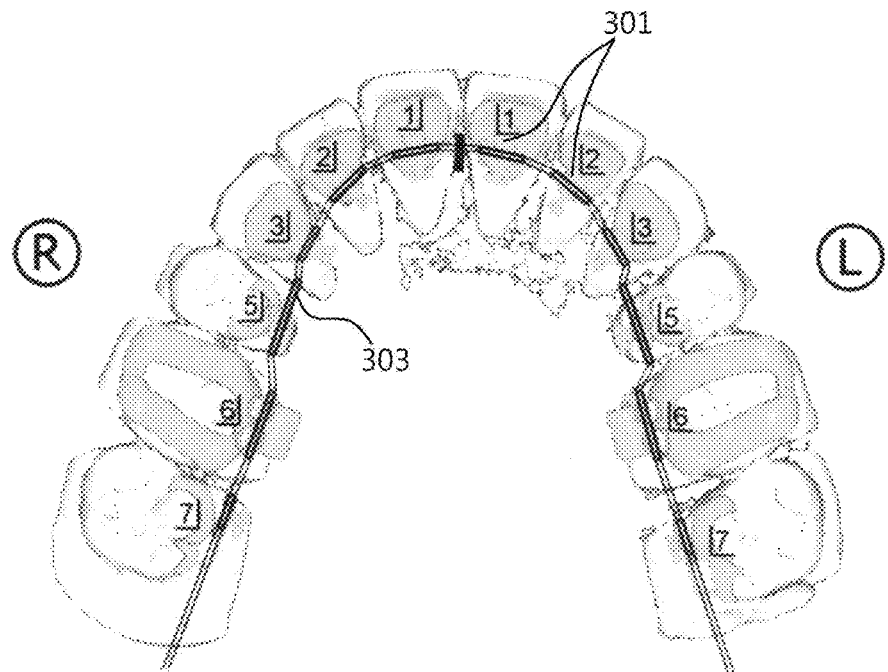
Figure 3B:
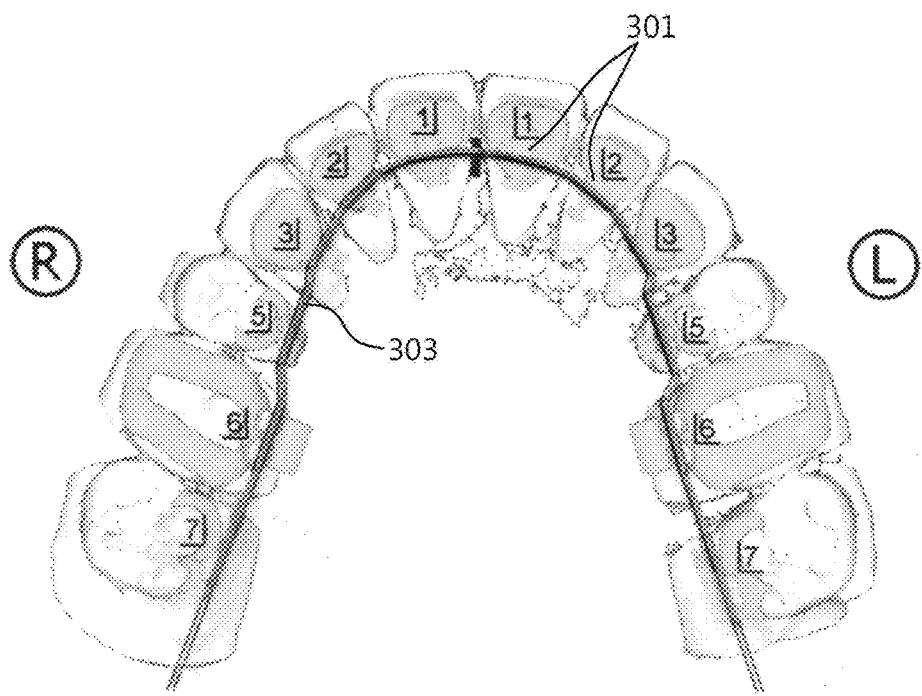
Figure 4A:
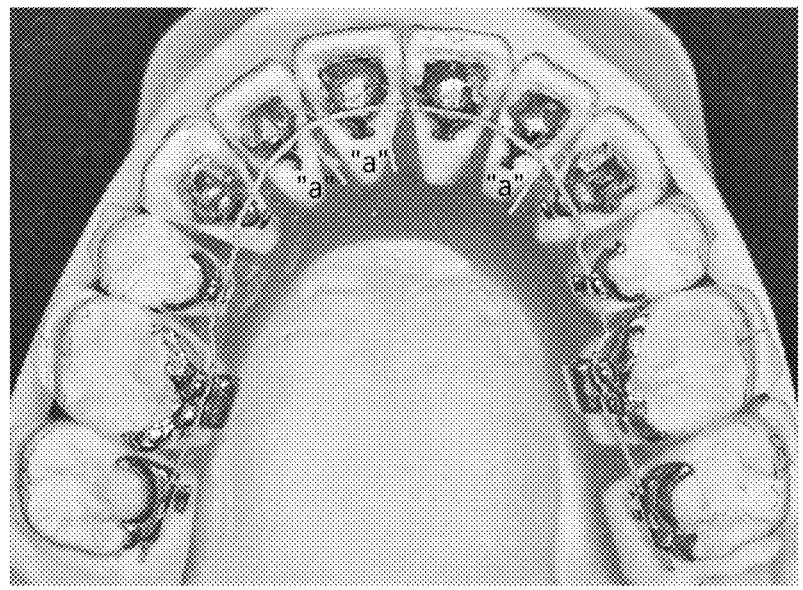
Figure 4B:
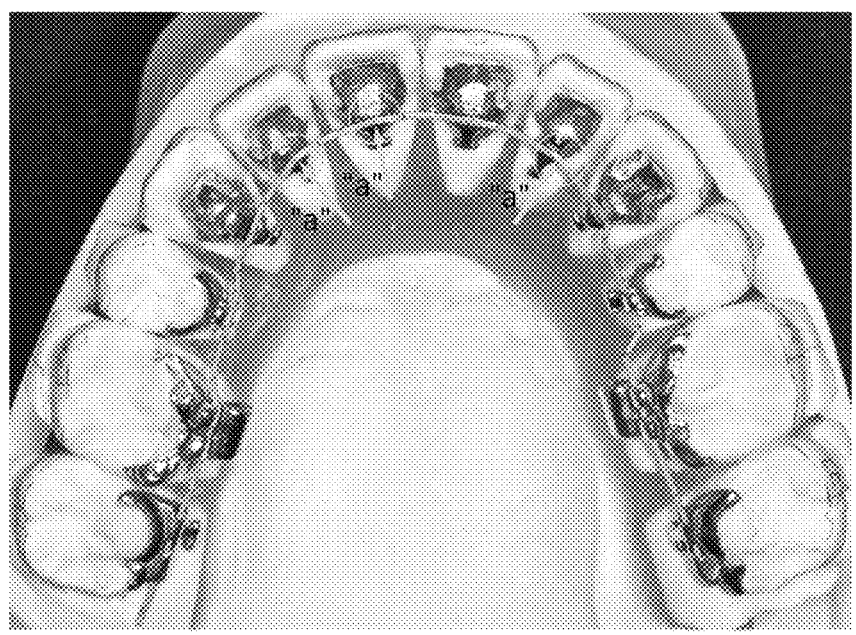

For example, as above-described in FIG. 1, in the related art in which the slot is disposed further away from the tooth surface, when only the degree of inclination of the tooth is adjusted, a serious problem in which heights of the incisal edges of neighboring teeth become different due to the rotation with the center of rotation at the slot may occur. That is, although the teeth are aligned at a height at which the orthodontic bracket is bonded, the incisal edge or the cusp tip may not be aligned requiring additional adjustment.

Contrast to this, according to the present invention, although the rotational moment M of the tooth occurs in a state in which the arch wire 60 is disposed to closely approach the tooth surface, the center of the rotation is disposed to closely approach the tooth surface to minimize height difference 'b' of the incisal edges between the neighboring teeth. Accordingly, since vertical and antero-posterior positions of the incisal edge are also aligned to maximally approach a position corresponding to a tooth root of the tooth after the ideal orthodontic treatment, the alignment of the teeth are performed together with alignment of teeth roots. Thus, the ideal orthodontic treatment is further easily performed.

Meanwhile, the arch wire 60 may have a curvature section in at least a front tooth section that is a section between both right and left canine teeth, and sections of posterior teeth may be formed as a linear section. This is desirable especially when the arch wire 60 is disposed on the lingual side of dental arch.

Also, when the arch wire is disposed on the labial side of the dental arch, entire section of the arch wire may be generally formed as the curvature section Of course, the arch wire may have a shape having only the curvature section on both labial and lingual sides of dental arch according to the individual dental arch form.

Figure 10:
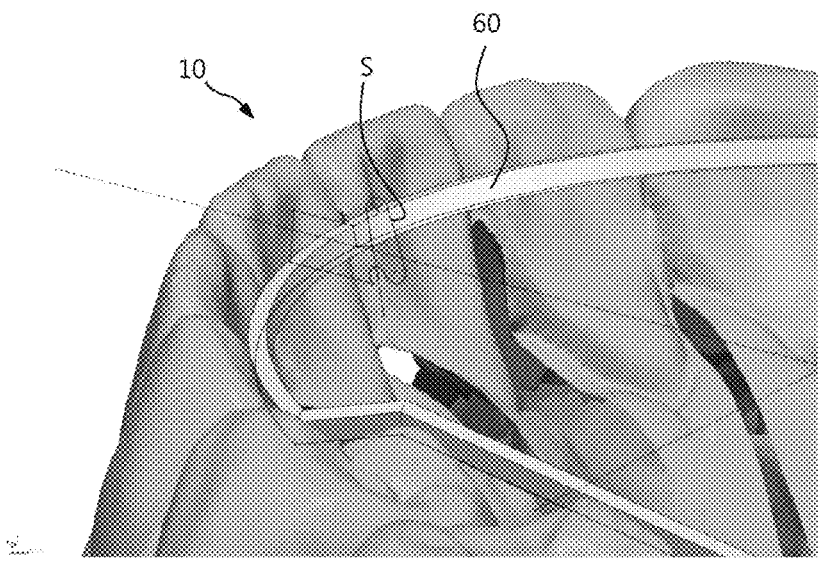
Figure 11:
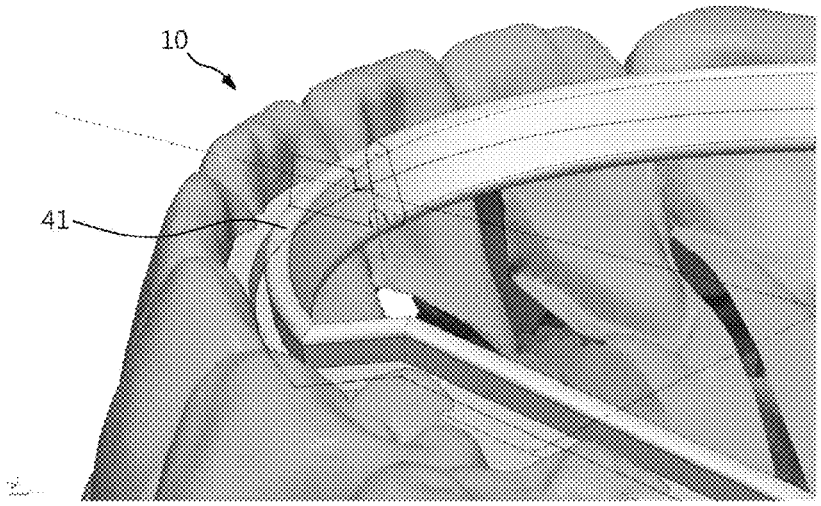
Figure 12:
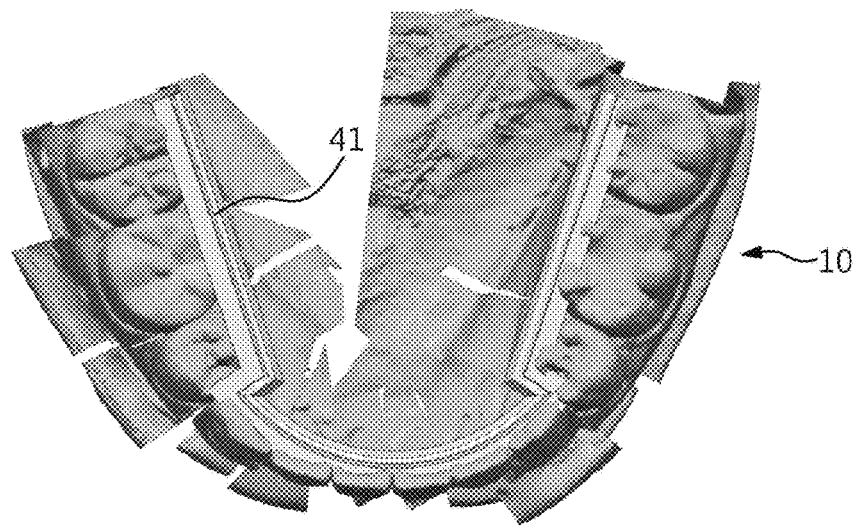
Figure 13:
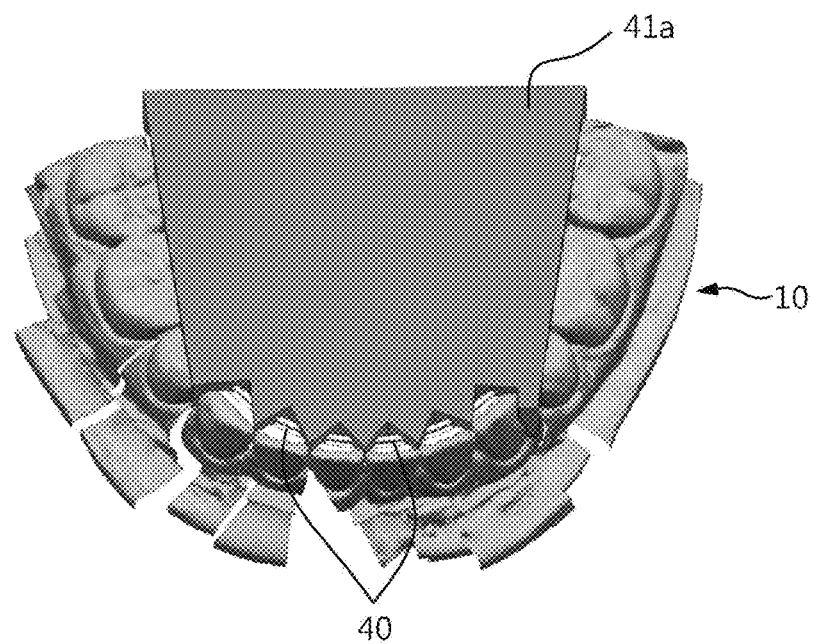
Figure 14:
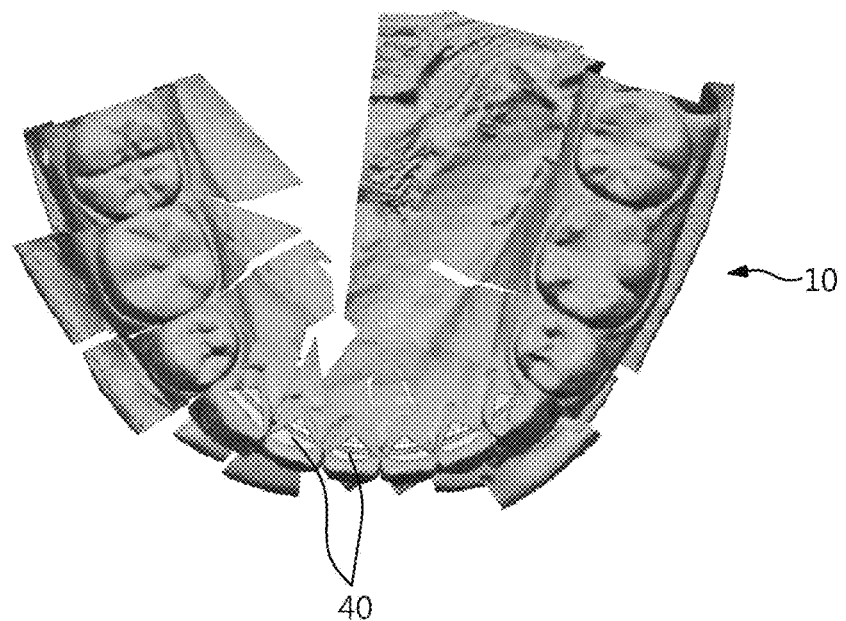
Figure 15:
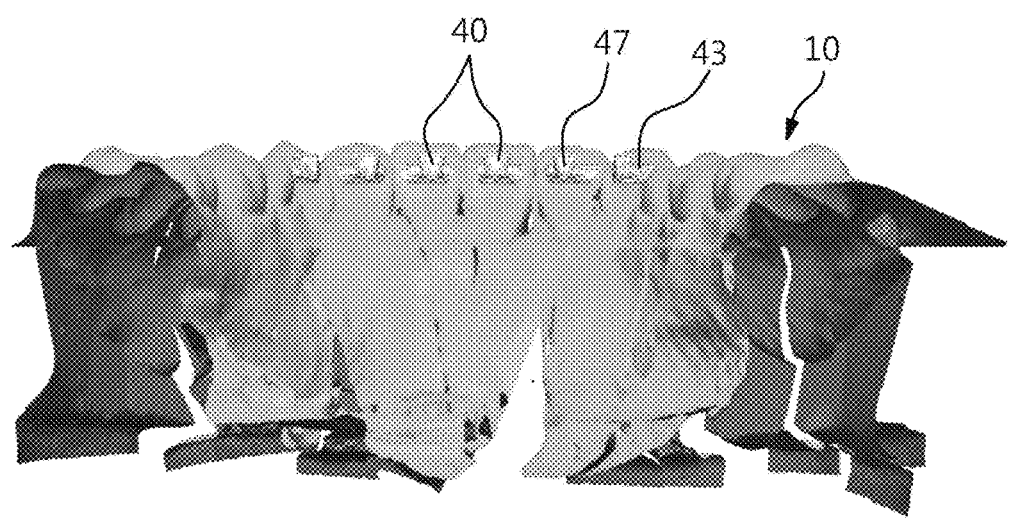

Meanwhile, the orthodontic bracket forming step S03 may include a bracket body block forming step S03a of forming the bracket body block 41 along an entire section of the arch wire 60 as illustrated in FIGS. 10 to 12, and a bracket body forming step S03b of forming each of the bracket bodies 40 corresponding to each tooth from the bracket body block 41 as illustrated in FIGS. 13 to 15.

As in FIG. 10, the bracket body block forming step S03a may be performed using a sketch 'S' of an approximately shaped cross-section of the bracket body 40 and the arch wire 60. By this method, a single 3D bracket body block 41 contacting tooth surfaces of all teeth along the entire length of the arch wire 60 is produced as in FIGS. 11 and 12.

The bracket body forming step S03b is a step of forming the bracket body block 41 into each of the bracket bodies 40 corresponding to each tooth. As in FIG. 13, the virtual bracket cutting block 41a having a bracket body cutting structure corresponding to each of the bracket bodies 40 is formed, and then, as in FIGS. 13 and 14, the bracket cutting block 41a is used to cut the bracket body block 41 by the Boolean cut and form the bracket body 40 corresponding to each of the teeth. Only the anterior tooth section between right and left canine teeth was illustrated in the drawings for convenience for description and illustration.

The above-described bracket body forming step S03b desirably includes a step of rounding an edge portion of each of the cut bracket bodies 40 as in FIG. 15. This rounding process prevents irritating sensation and injury caused by the bracket body 40 in the oral cavity As in FIGS. 20A to 20C, the bracket body 40 formed as above-described may have a bonding surface 30 bonded to the tooth surface without a separate base structure because a surface of the bracket body 40, which faces the tooth surface as in FIG. 20B, can be formed by removing the corresponding tooth T in the manner of the Boolean cut as in FIG. 20C.

Figure 16:
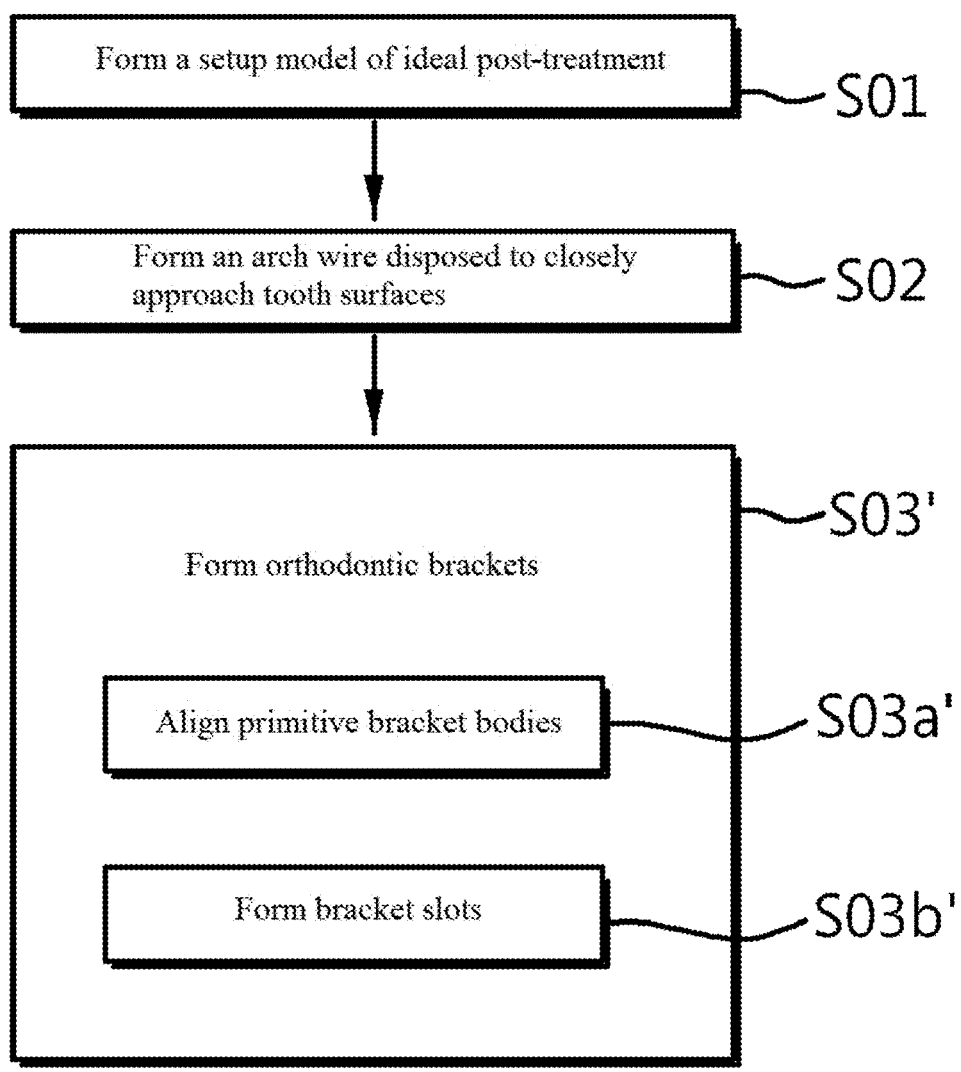
FIGS. 16 to 24 are views for explaining a method of fabricating an orthodontic appliance according to another embodiment of the present invention.

As in FIG. 16, an orthodontic bracket forming step S03' according to another embodiment of the present invention may include a primitive bracket body alignment step S03a' of producing virtual 3D primitive bracket bodies 42 to be respectively fit to positions corresponding to the arch wire 60 disposed to closely approach each of the teeth to align the primitive bracket bodies; and a slot forming step S03b' of forming a slot corresponding to the arch wire 60 in each of the primitive bracket bodies 42.

Figure 17:
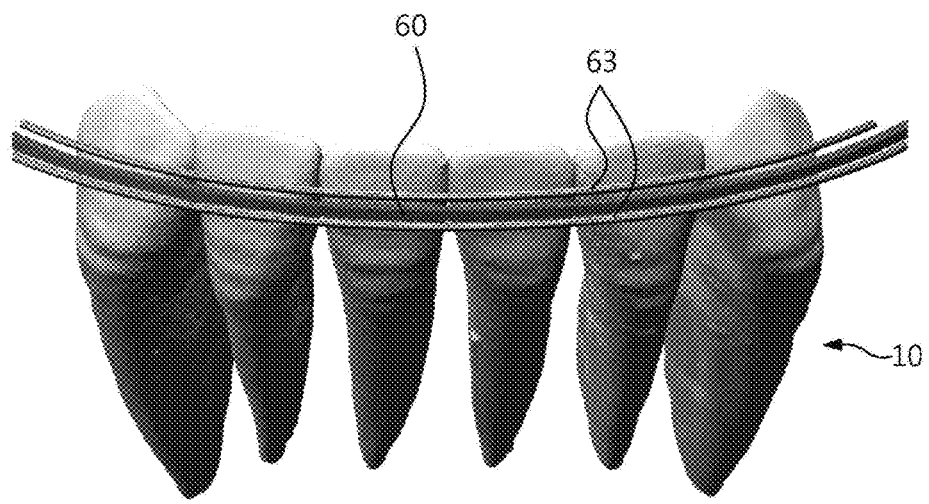
Figure 18:
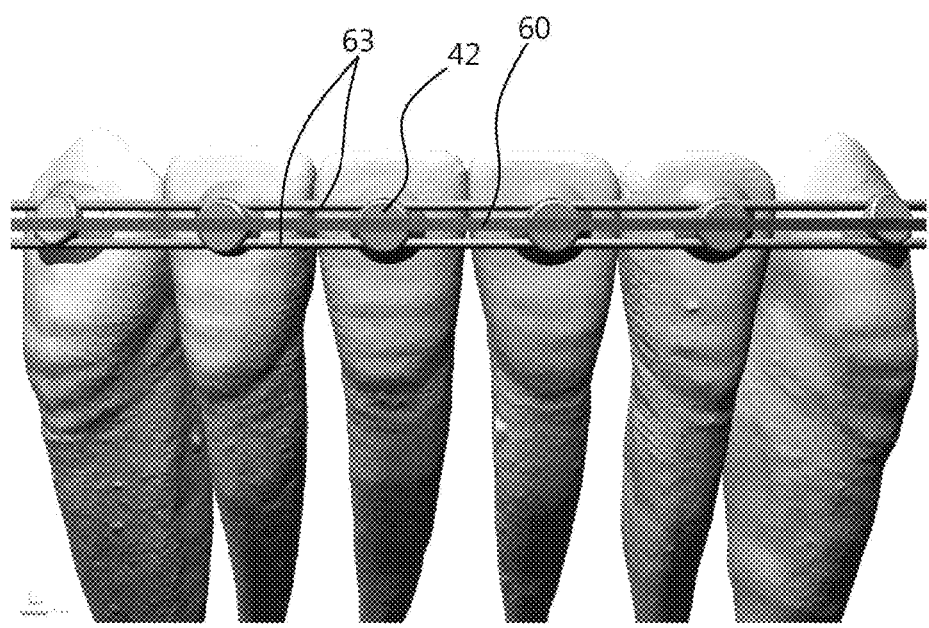

In labial orthodontic appliance as in FIGS. 17 and 18, the primitive bracket body alignment step S03a' may be performed such that the virtual 3D primitive bodies 42 respectively corresponding to the teeth are produced and are aligned on the computer with reference to the arch wire 60 disposed to closely approach the tooth surface of each of the teeth of the setup model 10 in the above-described arch wire forming step S02. Here, a height of the virtual primitive bracket body 42 may be varied depending on a vertical length of a crown of the patient and an occlusion contact state of occluded teeth.

Figure 19:
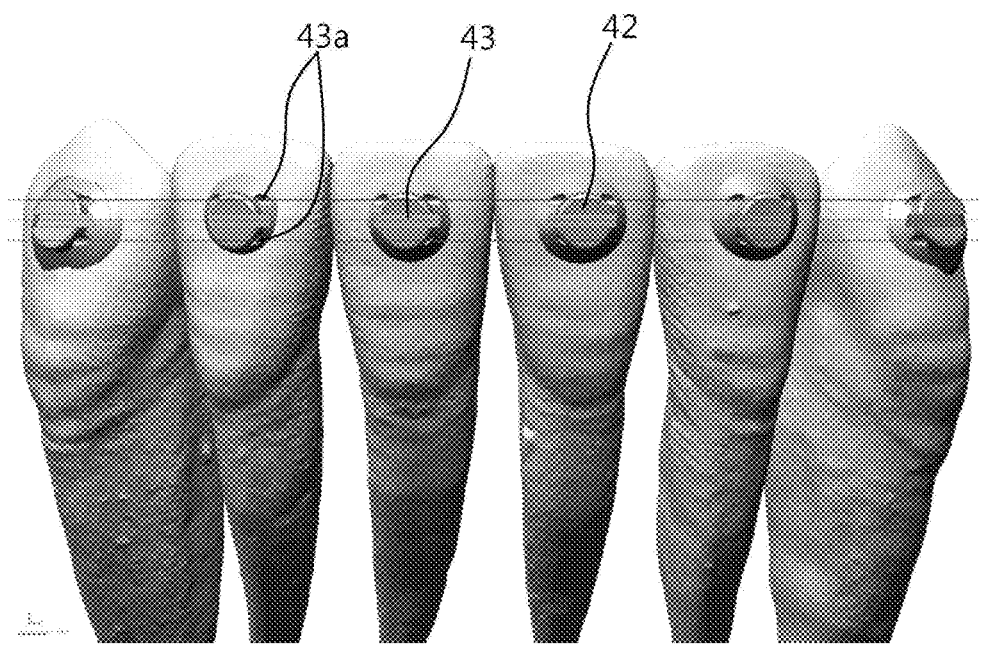

As illustrated in FIGS. 18 and 19, the slot forming step S03b' is performed such that the virtual slot 43 to which the arch wire is inserted is formed in the virtual 3D primitive bracket body 42 formed in the bracket body alignment step S03a' by using the manner of the Boolean cut removing the arch wire 60 on the computer.

Figure 23:
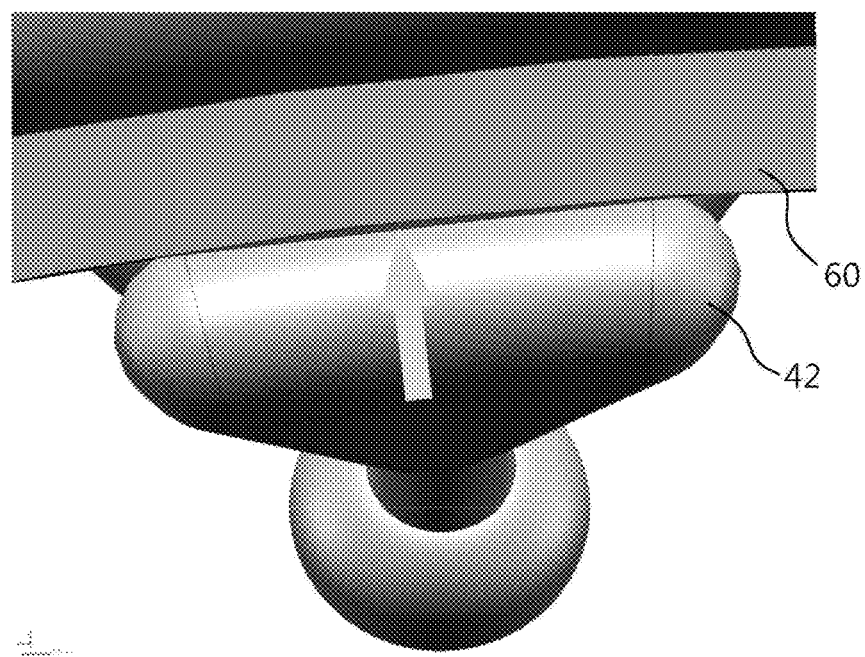

Here, in case of the lingual orthodontic treatment, like FIG. 23, the slot 43 is formed as a slot having a curvature corresponding to the arch wire 60 or a slot of which a lingual side wall of the slot, which corresponds to the curvature of the arch wire 60 is linearized (i.e., a straight line is formed between the both edges).

In general, the labial bracket (i.e., the orthodontic bracket bonded to the outer surface of the tooth) uses an edgewise slot. The edgewise slot represents the bracket slot into which the arch wire is horizontally inserted, and a ribbon arch slot represents the bracket slot into which the arch wire is vertically inserted. In general, when the labial edgewise orthodontic bracket is used, the arch wire contacts only left and right ends of the linear bracket slot.

There are two kinds of lingual orthodontic brackets. One uses the edgewise slot and the other uses the ribbon arch slot. In case of the lingual orthodontic bracket using the edgewise slot, since only a central point of the arch wire inserted into the slot contacts the bracket slot, rotation of the tooth is difficult to be adjusted.

In case of the lingual orthodontic bracket using the ribbon arch slot, friction between the linear bracket slot and the arch wire having a curvature may increase, and the arch wire may be straightened in the linear slot to deform a shape of the dental arch.

In case of the labial orthodontic bracket, since the arch wire has a great curvature and the contact occurs at only two points, the difference between the curvatures of the slot and the arch wire may be overcome. However, in case of the lingual orthodontic bracket, since the arch wire has a small curvature, the difference between the curvatures of the slot and the arch wire may cause a problem, and particularly in case of the lingual ribbon arch slot, the above-described problem caused by the difference between the curvatures occurs at both the labial side wall and the lingual side wall, which constitute the slot. Thus, in particular, the ribbon arch slot of the lingual orthodontic bracket is desirably formed to have the curvature that is the same as that of the arch wire.

Since the arch wire is designed in a cast state in which the alignment of the teeth is completed, the arch wire accurately corresponds to the slot after the teeth are completely aligned. The curvatures of the slot and the arch wire may not be accurately matched during the treatment step, and in case of this, friction between the arch wire and the slot may increase. To minimize the above-described problem, the lingual side wall that is a wall, which protrudes toward the slot, of the labial side wall and the lingual side wall, which constitute the ribbon arch slot, is linearized, and only outermost two points are disposed on the curvature of the arch wire. As the lingual side wall of the slot is linearized as described above, the friction between the protruding surface of the lingual side wall and the arch wire, which may occur when the arch wire has the curvature greater than that of the bracket slot, may be reduced.

Figure 20A:
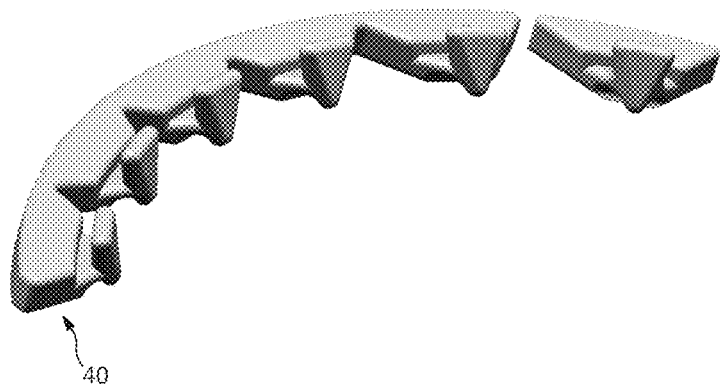
Figure 20B:
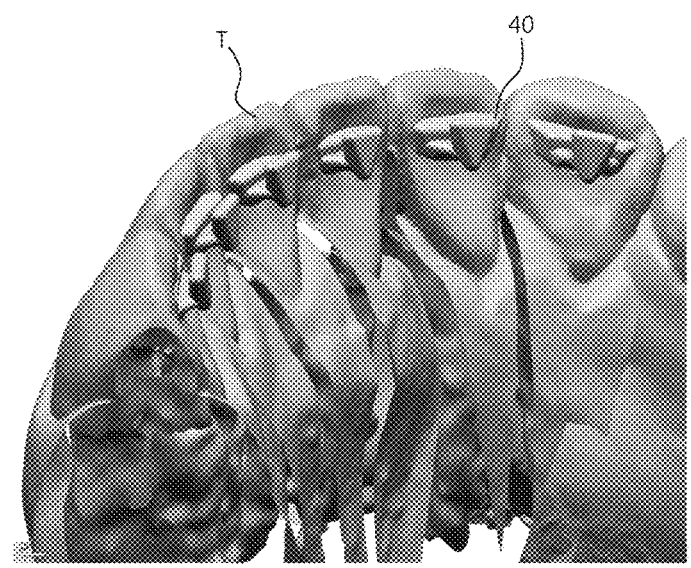
Figure 20C:
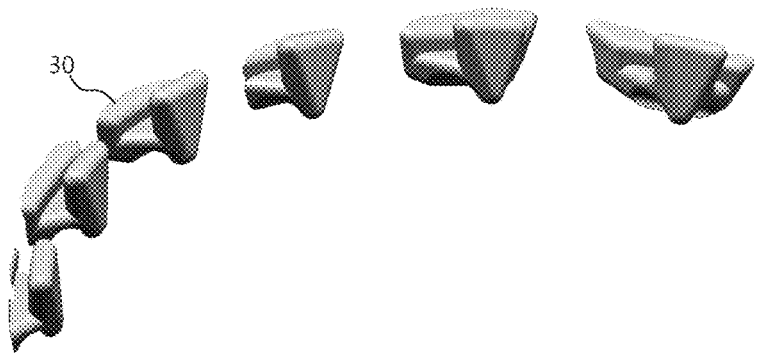

The surface of the bracket body 40, which is formed to face the tooth surface as above-described in FIG. 20A, is formed such that the corresponding tooth is removed in the manner of the Boolean cut as in FIG. 20C to be formed as the bonding surface 30 naturally bonded to the tooth surface without the separate base structure.

Referring to the bonding surface 30 in more detail, a portion of the bracket body 40, which overlaps the tooth, is removed in the manner of the Boolean cut to naturally form the bonding surface on a side of the bracket body 40, which faces the tooth.

The above-described bonding surface 30 forming method is extremely important when the arch wire 60 is disposed to closely approach the tooth surface not to provide a space for forming a separate base like the present invention.

Here, all conventional orthodontic brackets include the bracket body and the separate base due to concern in which when the bracket body directly contacts the tooth surface without the base, a bonding area may be too small to secure bonding force, and when the bracket body directly protrudes from the tooth surface, food leftovers may be stacked on a boundary surface between the tooth and the bracket body.

However, the above-described concern may be overcome by forming the bonding surface on a tooth side of the bracket body without the base and fabricating the bracket body to have a shape gradually expanding toward the tooth like an embodiment according to the present invention in FIG. 19.

In real fabrication process, when the bracket body is semi-processed by using a method such as a metal injection molding, and then the bonding surface is additionally cutting-processed by mechanical machining, a structure in which the bracket body is expanded is further appropriate to the mechanical machining than a structure in which the separate base is formed.

Of course, the bonding surface according to the present invention may be formed such that a separate bracket base 50 is formed on the tooth side portion of the bracket body 40 as in FIGS. 21A to 21D. This may be performed through an additional bracket base forming step.

The bracket base forming step is a step of fabricating the customized bracket base 50 corresponding to the tooth surface to provide the customized bracket base 50 corresponding to the tooth surface of the setup model 10 by using the computer-aided design and the rapid prototyping.

Figure 21A:
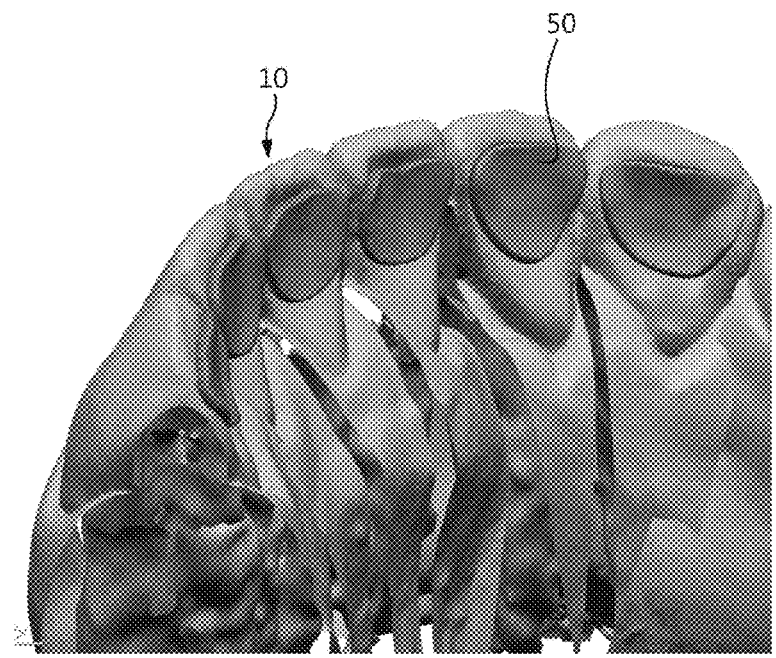
Figure 21B:
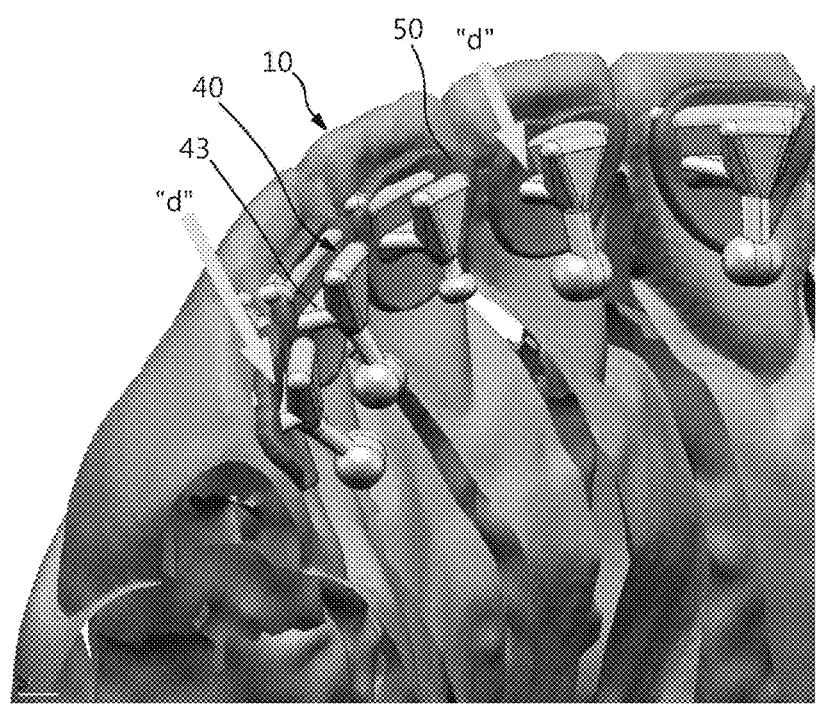

In the bracket base forming step, the bracket base 50 contacting the tooth surface is formed as a separate structure by using the above-described virtual 3D setup model 10 on the computer like FIG. 21A, and then coupled to the bracket body like FIG. 21B.

The bracket base 50 is fabricated to have a thickness equal to or greater than 0.3 mm. Here, since the arch wire 60 and the slot 43 are designed to be spaced by 0.3 mm or less from the tooth surface, the bracket base 50 is formed greater in thickness than the slot 43 in a portion like an arrow "d" in FIG. 21B, and the portion needs to be removed to mount the arch wire 60 on the slot 43.

Figure 21C:
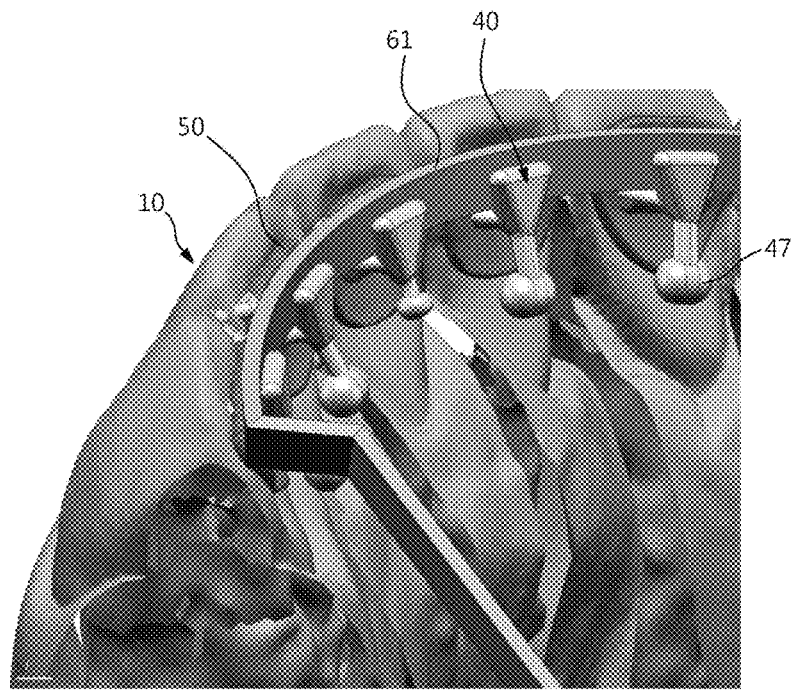
Figure 21D:
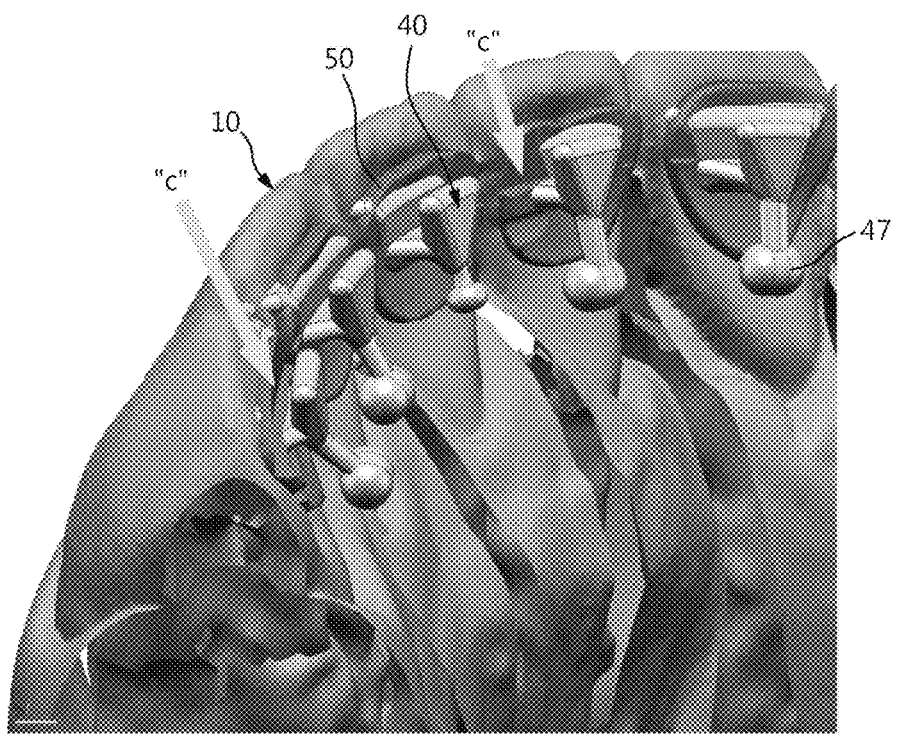
Figure 22:
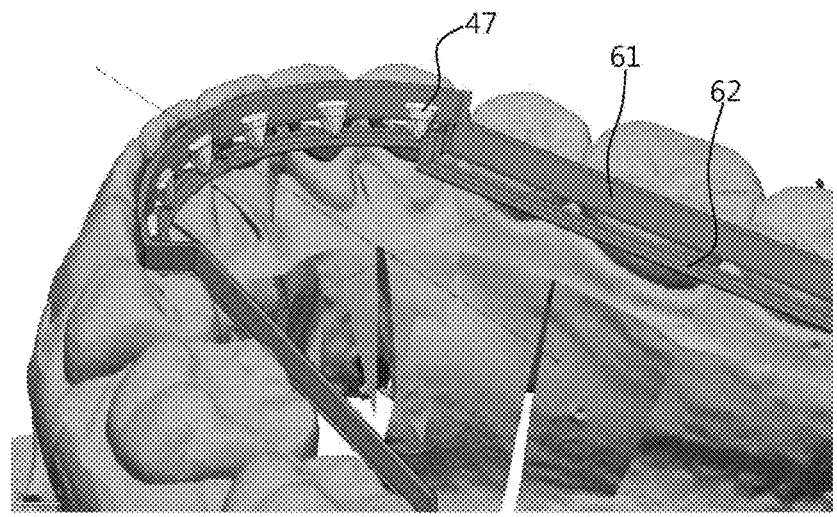

For this, as illustrated in FIGS. 21C and 22, it is desired to include a step of forming an arch wire insertion path (refer to an arrow "c" in FIG. 21D) on the bracket base 50 or the bracket base 50 and the bracket body 40 by the Boolean cut using an arch wire insertion path forming block 61. Also, since the bracket base 50 may prevent a ligature member (not shown) for ligating the arch wire 60 to the orthodontic bracket from being downward inserted into the bracket wing 47, like FIG. 22, a portion in which the bracket base intruding into a ligature member insertion path is removed to secure the ligature member insertion path so that the ligature member insertion path is not blocked by the bracket base 50. As a result, like an arrow "c" portion in FIG. 21D, the bracket base 50 is formed such that the slot 43 is additionally formed on the bracket base 50. The slot 43 extending up to a portion of the bracket base 50 may increase a contact distance between the arch wire 60 and the slot 43 to increase a distance between orthodontic coupling forces generated between the arch wire 60 and both ends of the slot 43, thereby further easily adjusting the tooth.

The rapid prototyping is used on the basis of the virtual bracket body 40 formed as above-described to provide the real bracket body optimized to each of the teeth of the patient.

Here, although it is desired to mold the real bracket body integrally with the real bonding surface, the real bracket body and the real bonding surface may be separately molded and then bonded to each other.

Here, like FIGS. 15 and 17 to 19, a ligature groove 43a having a structure in which a ligature line (not shown) for fixing the arch wire inserted into the slot 43 is ligated may be formed on at least one side of upper and lower portions of the real bracket body 40.

Here, the ligature groove 43a may be pre-formed on a real molded product of the real bracket body (not shown). Alternatively, the ligature groove 43a may not be formed on the real bracket body (not shown).

Meanwhile, in case that the ligature groove 43a is not formed on the bracket body 40, a ligature groove forming step of forming the ligature groove 43a on the bracket body 40 may be provided.

Like FIGS. 17 to 19, the forming of ligature groove 43a may be performed together in a step of enabling the arch wire to be disposed to closely approach the tooth surface.

The ligature groove 43a may be also formed by the manner of the Boolean cut using the ligature groove forming block 63 on the computer like the arch wire or ligature member insertion path forming step, and, on the basis of this, the real ligature groove may be formed on the real bracket body (not shown) by using mechanical machining.

Here, the forming of the ligature groove 43a by the Boolean cut may be performed such that when the bracket is formed as a tube type orthodontic bracket, the virtual 3D ligature groove forming block 63 is formed as in FIGS. 17 to 19, and when formed as a general orthodontic bracket, the virtual 3D ligature groove forming block 63 is formed as in FIG. 22, and then a region corresponding to the virtual ligature groove forming block 63 is removed from the virtual bracket body 40 to form the ligature groove 43a.

Figure 24A:
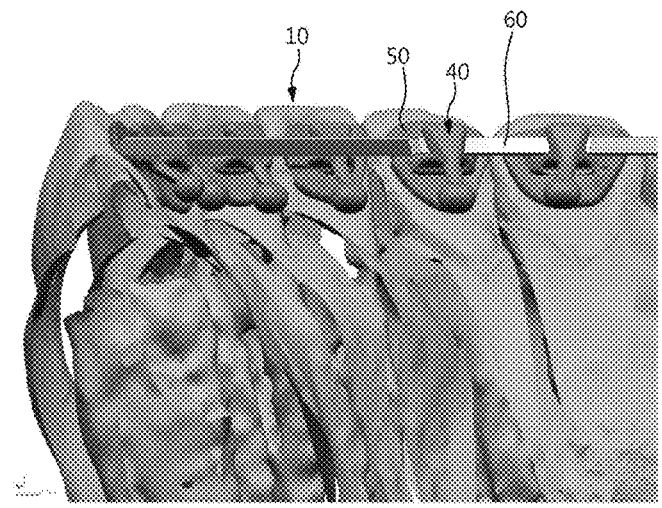
Figure 24B:
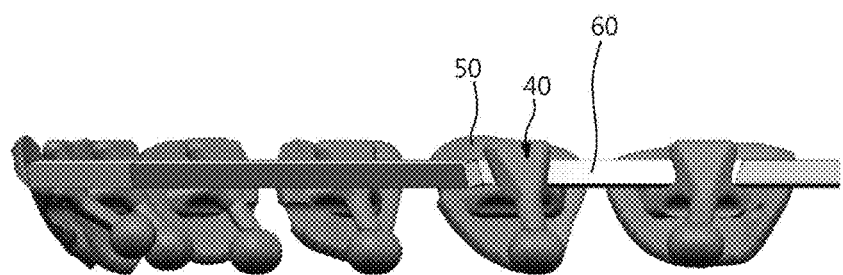
Figure 24C:
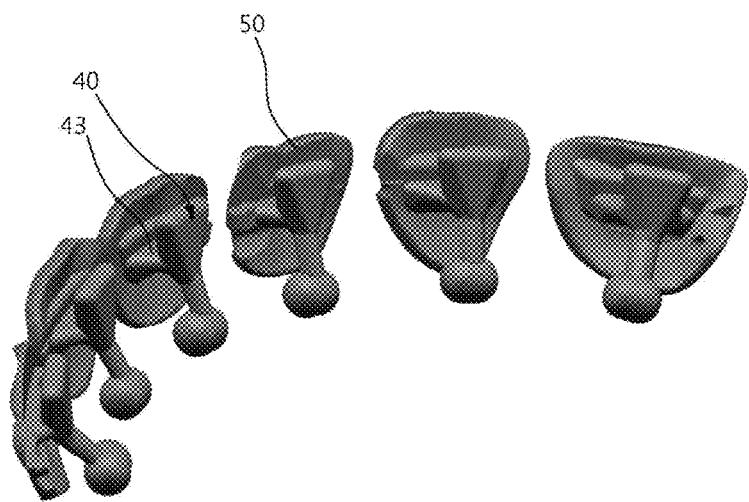

The orthodontic appliance fabricated by the above-described fabrication method according to the present invention may fabricate the setup model 10 showing the post-treatment occlusion, form the arch wire 60 disposed to maximally approach the tooth surface of the teeth realigned to the orthodontic position as in FIG. 24A, and fabricate the bracket body 40 with reference to the arch wire 60 as in FIG. 24B, so that the distance in which the slot 43 is spaced from the tooth surface is less than the thickness of the bracket base 50 even when the bracket base 50 is formed as in FIG. 24C and although the rotational moment of the tooth occurs during the orthodontic treatment, the unnecessary tooth incisal edge or position difference between the cusp tips is minimized regardless of whether the bracket base 50 is provided or not. Thus, the ideal orthodontic treatment may be accurately performed.

Also, as the bracket body 40 having the bonding surface accurately fit to the geometric structure of the tooth surface is fabricated regardless of whether the bracket base 50 is provided or not, the bonding surface of the orthodontic appliance may be easily and accurately bonded to the tooth surface of the patient during the procedure for the orthodontic appliance regardless of a tooth state before the orthodontic treatment for the patient.

As the bonding surface is bonded to the tooth surface of the patient as described above, the slot of each of the bracket bodies may be naturally positioned to correspond to the ideal arch wire formed by using the curvature of the setup model, and thus, as described above, the ideal arch wire fabricated to fit to the setup model may be accurately and easily inserted into the slot of the bracket body. The arch wire inserted into the slot ligates the separate ligature line to the ligature groove or the bracket wing and thus is fixed to the bracket body.

Here, as the slot is formed to have the curvature or straight line corresponding to the arch wire, the arch wire is accurately fit to and inserted into the slot. That is, when all of the slots of the bracket body are viewed from a plane, as each of the slots corresponds to the curvature of the arch wire or the straight line, the arch wire is accurately shape-matched to the slot.

Accordingly, the teeth before the orthodontic treatment for the patient may be forcedly orthodontic-treated to a position corresponding to the teeth after ideal orthodontic treatment.

Also, as the bracket body is formed in a state in which the arch wire is disposed to maximally approach the tooth surface of the patient, the height and volume of the bracket body may be prevented from unnecessarily increasing to be minimized. As a result, the irritating sensation in the oral cavity may be minimized.

As described above, according to the present invention, provided are the method of fabricating the customized orthodontic appliance capable of minimizing the distance between the tooth surface and the arch wire to perform the ideal orthodontic treatment and the customized orthodontic appliance fabricated by the same.

Also, provided is the method of fabricating the customized orthodontic appliance capable of significantly improving the convenience and accuracy of the procedure and minimizing the irritation sensation in the oral cavity and the customized orthodontic appliance fabricated by the same.

The present invention may be used for orthodontic treatment for a dental patient.

The invention claimed is:

1. A method of fabricating a customized orthodontic appliance, the method comprising:
    forming a virtual setup model corresponding to teeth after ideal orthodontic treatment for a patient;
    forming a virtual arc wire corresponding to a dental arch of the virtual setup model and placing the virtual arch wire close to tooth surfaces of the teeth; and
    forming a virtual single bracket body block along an entire section of the virtual arch wire;
    forming virtual bracket bodies respectively corresponding to each tooth from the virtual single bracket body block; and
    forming the customized orthodontic appliance of real bracket bodies corresponding to the virtual bracket bodies.

2. The method according to claim 1, wherein the formation of the virtual bracket bodies comprises:
forming a bracket cutting block having a body forming structure corresponding to each of the virtual bracket bodies; and
cutting the virtual single bracket body block by using the bracket cutting block to form each of the virtual bracket bodies.

3. The method according to claim 2, further comprising a step of removing a portion corresponding to the virtual arch wire from the virtual single bracket body to form a bracket slot.

4. The method according to claim 1, further comprising a step of removing a portion corresponding to the virtual arch wire from the virtual single bracket body block to form a bracket slot.

5. The method of claim 1, wherein the virtual arch wire is disposed to closely approach the tooth surface in a range of 0.01 mm to 0.3 mm.

6. The method according to claim 5, further comprising a step of forming at least one of a ligature groove, to which a ligature wire for fixing a real arch wire is ligated, or a bracket wing in the bracket body.

7. The method of claim 1, further comprising a step of removing a portion at which the virtual bracket body overlaps the virtual setup model to form a bonding surface corresponding to the tooth surface of each of the teeth of the virtual setup model on a side of each of the virtual bracket bodies, which faces the tooth surface.

8. The method of claim 1, further comprising a step of forming a separate bracket base corresponding to the tooth surface on a side of each of the virtual bracket bodies, which faces the tooth surface.

9. The method according to claim 8, wherein a minimum distance between the virtual arch wire and the tooth surface is less than a thickness of the virtual bracket base.

10. The method according to claim 9, further comprising removing a portion in which the thickness of the bracket base intrudes to the slot to form an arch wire insertion path.

11. The method according to claim 10, further comprising a ligature member insertion path forming step of removing a portion in which the thickness of the bracket base intrudes to a ligature member insertion path formed by a ligature groove, to which a ligature wire for fixing a real arch wire is ligated, or a bracket wing in the bracket body.

12. A method of fabricating a customized orthodontic appliance, the method comprising:
forming a virtual setup model corresponding to teeth after ideal orthodontic treatment for a patient;
forming a virtual arc wire corresponding to a dental arch of the virtual setup model and placing the virtual arch wire close to tooth surfaces of the teeth;
after placing the virtual arch wire, forming and aligning primitive bracket bodies respectively corresponding to each tooth at a position corresponding to the virtual arch wire; and
forming a slot corresponding to the virtual arch wire in each of the primitive bracket bodies,
wherein each slot has a same size; and
forming the customized orthodontic appliance of real bracket bodies corresponding to the virtual bracket bodies.

\* \* \* \* \*